United States Patent [19]

Kolter et al.

[11] Patent Number: 5,840,769
[45] Date of Patent: Nov. 24, 1998

[54] DIRECT TABLETTING AIDS

[75] Inventors: Karl Kolter, Limburgerhof; Siegfried Lang, Ludwigshafen; Peter Schmidt, Tuebingen; Anja Hühne, Tübingen, all of Germany

[73] Assignee: BASF Aktiengesellschaft, Ludwigshafen, Germany

[21] Appl. No.: 888,542

[22] Filed: Jul. 7, 1997

[30]  Foreign Application Priority Data

Jul. 16, 1996 [DE] Germany .................. 196 28 617.4

[51] Int. Cl.$^6$ ..................... A61K 47/00; A61K 47/32
[52] U.S. Cl. ........................ 514/781; 514/772.5
[58] Field of Search ................. 514/781, 772.5

[56]  References Cited

U.S. PATENT DOCUMENTS

| | | |
|---|---|---|
| 3,933,766 | 1/1976 | Hofmann et al. . |
| 4,693,750 | 9/1987 | Bauer et al. . |
| 5,006,345 | 4/1991 | Lang . |

FOREIGN PATENT DOCUMENTS

| | | |
|---|---|---|
| 1336687 | 8/1995 | Canada . |
| 273 209 | 7/1988 | European Pat. Off. . |
| 2 255 263 | 5/1974 | Germany . |
| 35 06 276 | 4/1986 | Germany . |
| 35 05 433 | 8/1986 | Germany . |

OTHER PUBLICATIONS

Ullmanns Enc., Band 19, 385–389.
Cellulose–Chemie, 13 (1932) 58–65 and 71–74.
Kaufmann et al., Angew. Makromol. Chem., 45 (1975) 167–175.

Primary Examiner—Raymond Henley, III
Attorney, Agent, or Firm—Keil & Weinkauf

[57]  ABSTRACT

Direct tabletting aids

A) 75–98% by weight of a powdered cellulose suitable for tabletting

B) 1–15% by weight of soluble polyvinylpyrrolidone

C) 0.5–10% by weight of crosslinked insoluble polyvinylpyrrolidone.

11 Claims, No Drawings

DIRECT TABLETTING AIDS

Direct tabletting aids

The invention relates to a direct tabletting aid comprising A) 75–98% by weight of a powdered cellulose suitable for tabletting, B) 1–15% by weight of soluble polyvinylpyrrolidone, and C) 0.5–10% by weight of crosslinked insoluble polyvinylpyrrolidone.

The invention furthermore relates to tablets which comprise such direct tabletting aids and to a process for producing the tablets using the direct tabletting aids according to the invention.

It is well known that the great majority of active substances cannot be compressed without the addition of ancillary substances. Thus, celluloses, especially microcrystalline celluloses, have long been used in the pharmaceutical industry as bulking agents and binders for direct tabletting.

Tabletting aids are required to have not only good flow properties and binding capacity but also a high uptake capacity for active substances which are difficult to compress. The resulting tablets are intended to have a short disintegration time, low friability, high fracture resistance and rapid release of active substance. Some of these requirements are contradictory: thus, for example, high fracture resistance is associated with the presence of many points of contact of the bulking agent and binder inside the tablet, which can be achieved only if the bulking agent and binder is in the form of fine particles. Fine-particle substances in turn have poor flow properties. Hence there has been no lack of attempts to improve or modify the bulking agents and binders so that these contradictory properties are substantially eliminated while retaining the beneficial characteristics. It is additionally intended that these modifications where possible have novel properties not present in the starting material, for example by having a disintegration-promoting effect in addition to their binding effect. Direct tabletting aids of this type, which are also referred to as multipurpose excipients, are, as a rule, preparations which are produced via specific processes, consist of a plurality of components and are also mentioned as coprocessed materials in the literature. Thus, for example, a combination of α-lactose monohydrate and powdered cellulose is disclosed for direct tabletting in DE-C 3 506 276. Although this composition has a high binding capacity, it has no disintegration-promoting properties, especially when the compressive forces are relatively high. Another combination of α-lactose monohydrate and polyvinylpyrrolidone as binder, and crosslinked, insoluble polyvinylpyrrolidone to promote disintegration, disclosed in DE-A 35 05 433, has excellent flow properties and results, without further addition of a disintegrant, in rapidly disintegrating tablets but is less suitable for high-dose active substances whose compressibility is poor, because the uptake capacity for active substances to form tablets with sufficient mechanical stability is limited.

It is an object of the present invention to develop a direct tabletting aid which, while having good flow properties and binding capacity to form rapidly disintegrating tablets of low friability and adequate hardness, has a high uptake capacity for active substances whose tablettability is poor.

We have found that this object is achieved by a direct tabletting aid (i.e. an aid which contains no active substances) which comprises the following mixture:

A) 75–98% by weight, preferably 89–93% by weight, of a powdered cellulose suitable for tabletting, B) 1–15% by weight, preferably 2–6% by weight, of soluble polyvinylpyrrolidone, C) 0.5–10% by weight, preferably 2–5% by weight, of crosslinked, insoluble polyvinylpyrrolidone, where all the percentage data are based on the direct tabletting aid.

The carrier material which is preferably used is powdered cellulose, in particular microcrystalline cellulose. The average particle size of the cellulose is preferably in the range from 10 to 70 μm, particularly preferably 20 to 50 μm. In general, 90% of the cellulose particles are in the range from 1 to 125 μm.

Suitable as polyvinylpyrrolidone to be used as component B) in the mixture are the products conventionally used as binders for tablets. Polyvinylpyrrolidones of this type are described, for example, in Ullmann, 4th edition, volume 19, pages 385 to 386. In general, the polyvinylpyrrolidones have a K value of from 20 to 120. Particularly preferred polyvinylpyrrolidones according to the invention have a K value of from 70 to 100, in particular 85 to 95, determined by the Fikentscher method (Cellulosechemie 13 (1932) 58–65 and 71–74).

Component C) in the mixture is a crosslinked, insoluble polyvinylpyrrolidone. The preparation and properties of crosslinked, insoluble polyvinylpyrrolidone, i.e. a product which is no longer soluble in water but is now only swellable in water, are described in detail in DE-A 22 55 263 and by H. F. Kaufmann & J. W. Breitenbach, Angew. Makromol. Chem., 45 (1975) 167–175.

The mixtures of components A), B) and C) according to the invention can be prepared in a conventional way, e.g. by wet granulation by conventional methods such as mixer granulation, Shugi granulation, extrusion, perforated plate granulation or, preferably, fluidized bed granulation.

The procedure for fluidized bed granulation is, for example, such that a mixture of microcrystalline cellulose A) and crosslinked, insoluble polyvinylpyrrolidone C) is introduced into the fluidized bed which is sprayed at 20°–100° C. with an aqueous solution of component B). The resulting granules are dried in the fluidized bed.

It is also possible as an alternative to spray a mixture of microcrystalline cellulose, crosslinked insoluble polyvinylpyrrolidone and soluble polyvinylpyrrolidone with water and then dry it. A combination of the two procedures is also possible, i.e. part of the soluble polyvinylpyrrolidone is present in the bed, and the remainder is dissolved in water and sprayed on. 90% of the low-dust granule particles obtained by fluidized bed granulation are in the range 25–700 μm.

Care must be taken with the other possible production processes (mixer granulation, extrusion, perforated plate granulation) that porous granules are produced. This can be achieved by, on the one hand, not moistening the powder mixture too greatly, in order to avoid coalescence or agglomeration, and, on the other hand, choosing a low degree of compaction. This why a low energy input (low stirring speed) is normally used for mixer granulation, and a low pressure is used for extrusion and perforated plate granulation.

The mixture of the abovementioned tabletting aids in the stated mixing ratios has the following advantages:

Stable tablets are obtained with microcrystalline cellulose even with low compressive forces, but its flow properties on its own are poor. The addition of polyvinylpyrrolidone and binder both improves the flow properties due to the increase in particle size taking place during granulation, and increases the plasticity. The addition of crosslinked polyvinylpyrrolidone as disintegration aid in conjunction with the fluidized bed granulation surprisingly results in looser, freerflowing and easily deformable granules with a high uptake capacity for active substances.

Compared with the known technique of mixing and tabletting active substances with microcrystalline cellulose, crosslinked polyvinylpyrrolidone and water-soluble polyvinylpyrrolidone, as described in, for example, EP-A 273 209, a tabletting process using the direct tabletting aid according to the invention is distinguished by being a simple production process and having a wide range of applicability with regard to the active substance to be employed.

The following examples are intended to explain the invention in detail.

A. Production of the direct tabletting aids

The direct tabletting aid is produced by fluidized bed granulation. For this, water-soluble polyvinylpyrrolidone with a K value of 90 (Kollidon® 90 F., BASF) was dissolved in water to give the stated concentration (in % by weight). The microcrystalline cellulose was mixed with insoluble, crosslinked polyvinylpyrrolidone (Kollidon® CL, BASF) in the fluidized bed, and then the Kollidon solution was sprayed onto the powder bed under the following conditions:

Inlet air: 60° C.

Nozzle: 1.2 mm

Spray pressure: 2.5 bar

Spraying rate: see Table

Amount of air: 400 m³/h

The granules were dried in the fluidized bed. This resulted in the granule compositions compiled in the following table.

TABLE 1

|  | Granules A | Granules B | Granules C | Granules D |
|---|---|---|---|---|
| Microcrystalline Cellulose [% by wt] | 91.5 | 92.5 | 91.5 | 92.5 |
| Kollidon 90 F [% by wt] | 5.0 | 4.0 | 5.0 | 4.0 |
| Kollidon CL [% by wt] | 3.5 | 3.5 | 3.5 | 3.5 |
| Concentration of the Kollidon 90F solution [%] | 2.5 | 5.0 | 7.5 | 5.0 |
| Spraying rate [g/min] | 100 | 118 | 100 | 75 |

The angle of slope for the granules obtained in this way is 28°–33°.

B. Tabletting tests

The tabletting mixture was produced by screening the active substance through a No. 4 screen (800 μm) and loosely mixing it with the direct tabletting aid. Then 0.5% by weight of magnesium stearate was added through a No. 5 screen (315 μm), and the powder mixture was mixed for 10 minutes. The tabletting results were found using a pressure of 150 MPa.

Tables 2 and 3 show the tabletting results with the granules according to the invention (A to D) compared with experimental data with Ludipress® (consisting of 93% by weight of lactose, 3.5% by weight of Kollidon® 30 and 3.5% by weight of Kollidon® CL) and with Avicel® PH 200, a microcrystalline cellulose.

Tabletting test 1

| Ascorbic acid crystals | 40% by wt |
|---|---|
| Direct tabletting aid | 59.5% by wt |
| Magnesium stearate | 0.5% by wt |

TABLE 2

|  | Tensile Strength [MPa] | Friability [%] | Disintegration time [min] |
|---|---|---|---|
| Granules A | 1.5 | 0.29 | 0.7 |
| Granules B | 2.15 | 0.18 | 1.1 |
| Granules C | 2.1 | 0.14 | 1.2 |
| Granules D | 2.22 | 0.28 | 1.2 |
| Ludipress | 0.48 | 1.77 | 0.5 |
| Avicel PH 200 (Comp.) | 0.85 | 0.7 | 0.2 |

Tabletting test 2

| Paracetamol powder | 30% by wt |
|---|---|
| Direct tabletting aid | 69.5% by wt |
| Magnesium stearate | 0.5% by wt |

Table 3

TABLE 3

|  | Tensile Strength [MPa] | Friability [%] | Disintegration time [min] |
|---|---|---|---|
| Granules A | 1.48 | 0.34 | 0.2 |
| Granules B | 2.28 | 0.36 | 0.2 |
| Granules C | 2.35 | 0.1 | 0.3 |
| Granules D | 2.35 | 0.16 | 0.3 |
| Ludipress | 0.75 | 2.3 | 0.5 |
| Avicel PH 200 (Comp.) | 1.0 | 1.0 | 0.3 |

C. Determination of the uptake capacity for active substance paracetamol powder as example with granules B compared with Ludipress.

The tabletting mixture was produced as described above. The results were found with a pressure of 150 MPa. Addition of 0.5% Aerosil was necessary when the paracetamol powder content was 40% by weight and above because the active substance is not free-flowing and the flow properties of the tabletting mixture were greatly impaired.

TABELLE 4

|  | Tensile Strength [MPa] | Friability [%] | Disintegration time [min] |
|---|---|---|---|
| Ludipress |  |  |  |
| No active substance | 1.75 | 0.25 | 2.1 |
| 10% Paracetamol | 1.29 | 0.3 | 1.2 |
| 20% Paracetamol | 1.10 | 0.5 | 0.6 |
| 30% Paracetamol | 0.75 | 2.3 | 0.5 |
| 40% Paracetamol | 0.48 | 15.5 | 1.2 |
| Granules B |  |  |  |
| No active substance | 4.5 | 0.38 | 2.1 |
| 30% Paracetamol | 2.1 | 0.36 | 0.2 |
| 40% Paracetamol + 0,5% Aerosil | 2.4 | 0.22 | 0.2 |
| 50% Paracetamol + 0,5% Aerosil | 2.3 | 0.38 | 0.4 |

D. Examples of the tabletting of the physical mixture of microcrystalline cellulose, Kollidon 90 F and Kollidon CL, and the compacted mixture of microcrystalline cellulose, Kollidon 90 F and Kollidon CL compared with Granules B.

Compacted material was produced by compressing the powder mixture in a medium pressure range of 15–18 kN and was subsequently comminuted. The proportion which passed through an 800 μm screen was used for further processing. It is scarcely possible for the physical mixture to be tabletted because the flow properties are extremely poor. The standard deviations for pressure and weight are very large. The disintegration time of the resulting tablets is much greater than 15 minutes.

|  | Tensile Strength [MPa] | Friability [%] | Disintegration time [min] |
|---|---|---|---|
| Physical mixture without active substance | 8 | 0.1 | >>15 min |
| Physical mixture + 30% paracetamol powder | 3.8 | 0.15 | >>15 min |
| Compacted material without active substance | 0.35 | 100 | >15 min |
| Compacted material + 30% paracetamol powder | 0.2 | 100 | 2.6 |
| Granules B without active substance | 4.5 | 0.38 | 2.1 |
| Granules B + 30% paracetamol | 2.1 | 0.36 | 0.2 |
| Ludipress without active substance | 1.75 | 0.25 | 2.1 |
| Ludipress + 30% paracetamol | 0.75 | 2.3 | 0.5 |

We claim:

1. A direct tabletting aid comprising
   A) 75–98% by weight of a powdered cellulose suitable for tabletting
   B) 1–15% by weight of soluble polyvinylpyrrolidone
   C) 0.5–10% by weight of crosslinked insoluble polyvinylpyrrolidone.

2. A direct tabletting aid as defined in claim 1, wherein the powdered cellulose is microcrystalline cellulose.

3. A direct tabletting aid as defined in claim 2, wherein the microcrystalline cellulose is of a type in which 90% of the particles are in the range from 1 $\mu$m to 125 $\mu$m, and the average particle size is from 10 $\mu$m to 70 $\mu$m.

4. A direct tabletting aid as defined in claim 1, wherein the soluble polyvinylpyrrolidone has a K value of from 20 to 120.

5. A direct tabletting aid as defined in claim 1, wherein the soluble polyvinylpyrrolidone has a K value of from 25 to 95.

6. A direct tabletting aid as defined in any of claim 1, which is produced by wet granulation.

7. A direct tabletting aid as defined in claim 1, and in particulate form which is produced by fluidized bed granulation.

8. A direct tabletting aid as defined in claim 1, wherein 90% of the particles are in the range 25–700 $\mu$m.

9. A tablet which comprises a direct tabletting aid as defined in claim 1.

10. A process for producing tablets, which comprises compressing an active ingredient with the direct tabletting aid as defined in claim 1.

11. A direct tabletting aid as defined in claim 4, wherein the soluble polyvinylpyrrolidone has a K value of from 25 to 95.

* * * * *

UNITED STATES PATENT AND TRADEMARK OFFICE
CERTIFICATE OF CORRECTION

PATENT NO. : 5,840,769
DATED : November 24, 1998
INVENTOR(S) : KOLTER et al.

It is certified that error appears in the above-identified patent and that said Letters Patent is hereby corrected as shown below:

On the title page, Item [57]Abstract: "Direct tabletting aids" should read --A direct tabletting aid containing--.

Col. 6, claim 8, line 20, "claim 1" should be --claim 7--.

Col. 6, claim 10, line 26, delete "as".

Signed and Sealed this

Thirteenth Day of July, 1999

Attest:

Q. TODD DICKINSON

Attesting Officer

Acting Commissioner of Patents and Trademarks